United States Patent
Nagasuna et al.

(10) Patent No.: US 6,297,319 B1
(45) Date of Patent: Oct. 2, 2001

(54) WATER-ABSORBING AGENT AND PRODUCTION PROCESS THEREFOR

(75) Inventors: Kinya Nagasuna, Kitakatsuragi-gun; Shinichi Fujino; Masatoshi Nakamura, both of Himeji; Kunihiko Ishizaki, Suita, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/432,018

(22) Filed: Nov. 2, 1999

(30) Foreign Application Priority Data

Nov. 5, 1998 (JP) .................................................. 10-314351

(51) Int. Cl.⁷ .............................. C08F 8/00; C08L 33/00; C08L 47/00; C08L 53/00; C08L 61/00
(52) U.S. Cl. ......................... 525/96; 525/141; 525/142; 525/143; 527/201; 527/203; 527/204
(58) Field of Search ............................. 525/96, 141, 142, 525/143; 527/201, 203, 204

(56) References Cited

U.S. PATENT DOCUMENTS

| | | |
|---|---|---|
| 4,043,952 | 8/1977 | Ganslaw et al. . |
| 4,051,086 | 9/1977 | Reid . |
| 4,587,308 | 5/1986 | Makita et al. . |
| 4,666,983 | 5/1987 | Tsubakimoto et al. . |
| 4,734,478 | 3/1988 | Tsubakimoto et al. . |
| 4,755,560 | 7/1988 | Ito et al. . |
| 5,322,896 | 6/1994 | Ueda et al. . |
| 5,409,771 | 4/1995 | Dahmen et al. . |
| 5,610,220 | 3/1997 | Klimmek et al. . |
| 6,121,509 * | 9/2000 | Ashraf et al. ........................ 604/368 |

FOREIGN PATENT DOCUMENTS

| | | |
|---|---|---|
| 40 20 780 C1 | 8/1991 | (DE) . |
| 0 372 981 B1 | 6/1990 | (EP) . |
| 0 450 922 A2 | 10/1991 | (EP) . |
| 0 450 923 A2 | 10/1991 | (EP) . |
| 0 555 692 B1 | 8/1993 | (EP) . |
| 0 574 260 A1 | 12/1993 | (EP) . |
| 51-136588 A | 11/1976 | (JP) . |
| 52-117393 A | 10/1977 | (JP) . |
| 58-180233 A | 10/1983 | (JP) . |
| 59-189103 A | 10/1984 | (JP) . |
| 60-163956 A | 8/1985 | (JP) . |
| 60-255814 A | 12/1985 | (JP) . |
| 61-16903 A | 1/1986 | (JP) . |
| 61-211305 A | 9/1986 | (JP) . |
| 61-252212 A | 11/1986 | (JP) . |
| 61-257235 A | 11/1986 | (JP) . |
| 61-264006 A | 11/1986 | (JP) . |
| 62-7745 A | 1/1987 | (JP) . |
| 1-292004 A | 11/1989 | (JP) . |
| 2-153903 A | 6/1990 | (JP) . |
| 3-179008 A | 8/1991 | (JP) . |
| 6-278237 A | 10/1994 | (JP) . |
| 8-508517 A | 9/1996 | (JP) . |
| WO97/39780 A1 | 10/1997 | (WO) . |

* cited by examiner

Primary Examiner—Nathan M. Nutter

(57) ABSTRACT

The present invention provides: a process for producing a water-absorbing agent by using a crosslinking agent of high safety, wherein the water-absorbing agent is excellent in the absorption capacities under no load and under a load and further in the blocking ratio under a load, and can display excellent absorption properties even if the weight percentage of the water-absorbent resin (resin concentration) is high when the water-absorbent resin is used for materials such as sanitary materials; and such a water-absorbing agent. The water-absorbent resin is mixed and treated with an oxazoline compound, wherein the oxazoline compound has at least three structural units of general formula (1) below:

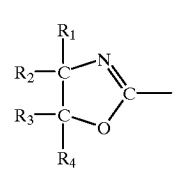

(1)

wherein $R_1$~$R_4$ separately denote a hydrogen atom, an alkyl group, an aromatic group, a halogen group, a substituted alkyl group, or a substituted aromatic group.

23 Claims, No Drawings

WATER-ABSORBING AGENT AND PRODUCTION PROCESS THEREFOR

BACKGROUND OF THE INVENTION

A. Technical Field

The present invention relates to: a production process for a water-absorbing agent which is favorably used for sanitary materials such as paper-made diapers (disposable diapers), sanitary napkins and so-called incontinent pads; and a water-absorbent resin (water-absorbing material) composition.

B. Background Art

In recent years, water-absorbent resins that are hydrophilic resins are widely used as constituent materials of sanitary materials, such as disposable diapers, sanitary napkins, and so-called incontinent pads, for the purpose of causing the water-absorbent resins to absorb body fluids.

Known examples of the above water-absorbent resins are as follows: crosslinked products of partially neutralized polyacrylic acids; hydrolyzed products of starch-acrylonitrile grafted polymers; neutralized products of starch-acrylic acid grafted polymers; saponified products of vinyl acetate-acrylic acid ester copolymers; hydrolyzed products of acrylonitrile- or acrylamide copolymers, and their crosslinked products; and crosslinked polymers of cationic monomers.

Examples of the properties which the above water-absorbent resins should have are as follows: upon contact with aqueous liquids such as body fluids, excellent water absorption amount or speed, the liquid permeability, the gel strength of the swollen gel, the suction power to suck up water from a base material containing aqueous liquids. However, relations between these properties do not necessarily display positive correlations. For example, as the absorption capacity under no load increases, the absorption properties under a load deteriorate.

As to a method for improving such water absorption properties (e.g. absorption capacities under no load and under a load) of the water-absorbent resin in good balance, there is a known art in which the neighborhood of the surface of the water-absorbent resin is crosslinked, and various methods have been proposed as such.

For example, there are known methods in which the following materials are used as the crosslinking agents: polyhydric alcohols (JP-A-58-180233 and JP-A-61-016903); polyglycidyl compounds, polyaziridine compounds, polyamine compounds, or polyisocyanate compounds (JP-A-59-189103); glyoxal (JP-A-52-117393); polyvalent metals (JP-A-51-136588, JP-A-61-257235 and JP-A-62-007745); silane coupling agents (JP-A-61-211305, JP-A-61-252212, and JP-A-61-264006); alkylene carbonates (DE 4020780). In addition, there are also known methods in which the following materials are allowed to be present as third substances for the purpose of improving the dispersibility of the crosslinking agent when the crosslinking agent is mixed or when the crosslinking reaction is carried out: inert inorganic powders (JP-A-60-163956 and JP-A-60-255814); dihydric alcohols (JP-A-01-292004); water along with ether compounds (JP-A-02-153903); alkylene oxide adducts of monohydric alcohols, organic acid salts, lactams, and so on (EP 555692); and phosphoric acid (Publication of Internal Patent Application as entered the national phase in Japan (Kohyo) No. 08-508517).

The production of various water-absorbent articles containing water-absorbent resins needs a step of combining a high hygroscopic resin with a fibrous material. Cases of the production of recently trendy water-absorbent articles, which use a large quantity of water-absorbent resin and are getting thinner and thinner, such as sanitary supplies, have more and more serious problems in that the efficient and stable production is impossible according to working environment and weather conditions, because the amount of the resin as added per piece of product is increasing. That is to say, resins of which the particles tend to block each other, therefore, of which the so-called blocking ratio under a load is high, have more and more serious problems in that: when a pressure is applied to particles of the resins under conditions of specific humidity, the resins easily cause blocking in hoppers or on the way of lines, therefore stable operation is difficult.

Such a blocking ratio under a load might have a tendency to worsen due to crosslinking the neighborhood of the surface of the above water-absorbent resin, and further has a tendency to be contradictory to the water absorption properties under a load.

Generally, examples of known methods of post-treatment to solve the blocking property of resins include: a composition as obtained by mixing a water-absorbent resin powder and a hydrophobic, finely particulate silica in a specific ratio (JP-B-61-017542); a composition as obtained by mixing a water-absorbent resin powder with an inorganic powder such as hydrous silicon dioxide, hydrous aluminum dioxide, and hydrous titanium dioxide (JP-A-59-080459); a method comprising the steps of treating a water-absorbent resin with a specific cationic surfactant and then mixing the treated resin with an inorganic substance or a high melting point organic compound (JP-A-61-069854); a method comprising the step of mixing a water-absorbent resin powder with stearic acid and an inorganic powder (JP-A-63-105064); and a method comprising the step of treating a water-absorbent resin with a specific silicone surfactant (JP-A-07-165981).

However, as to such resins with the improved blocking property, it has been found that the balance between the water absorption properties, such as absorption capacities under no load and under a load, particularly, absorption properties under a load, might be so low as to increase the amount of wet back in cases of absorbent articles having high resin concentration. In addition, there are also problems in that, generally, the post-treatment step for solving this blocking property is added to the surface-crosslinking step, therefore the production process becomes complicated.

Furthermore, there is a problem of the safety of the surface-crosslinking agent as used. Generally, in the case where the crosslinking agent is a low-molecular compound that has high reactive groups such as epoxy group, the water-absorbent resin as treated therewith has a relatively low blocking ratio under a load and therefore provides good results, but the crosslinking agent itself has property to stimulate skin. Thus, not only considering problems on environment of working, but also considering the application to sanitary materials, it is necessary to strictly control factors such as the amount of the crosslinking agent remaining in the resin, and further, complicated operations in the process are necessary also for decreasing the amount of the residual crosslinking agent. In addition, in the case where the crosslinking agent is a polyhydric alcohol, alkylene carbonate or the like, the crosslinking agent itself has relatively high safety, but some of them tend to increase the blocking ratio under a load, and further, have so low reactivity as the crosslinking agent that the reaction thereof needs a relatively high temperature and a long period of time. Therefore, during the crosslinking reaction, the water-absorbent resin might be degraded or the properties of the water-absorbent resin might be deteriorated.

Thus, in the actual state of things, there has never been an art (for obtaining water-absorbent resins as preferably used for sanitary materials) which is satisfactory with regard to the performance, the process, and the safety.

SUMMARY OF THE INVENTION

A. Objects of the Invention

The present invention was made considering the above problems on the prior arts, and an object of the present invention is to provide a production process for a water-absorbing agent which is excellent in the absorption capacities under no load and under a load and can display excellent absorption properties when used for materials such as sanitary materials, and further, which has a low blocking ratio under a load even without any especial post-treatment step and gives good workability even when combined into absorbent articles such as diapers so that the resin concentration will be high. Another object of the present invention is to provide a new crosslinking agent which has excellent safety and is particularly fit to treat water-absorbent resins. Yet another object of the present invention is to provide a water-absorbing agent of high safety which is a product by treatment with a specific compound as the above crosslinking agent and is excellent in the absorption capacities under no load and under a load and is favorably used for materials such as sanitary materials and is also excellent in the blocking ratio under a load.

B. Disclosure of the Invention

The present inventors diligently studied water-absorbing agents in view of achievement of the excellent water absorption properties under no load and under a load and the low blocking ratio under a load. As a result, the inventors completed the present invention by finding that the above objects all can be achieved if the water-absorbent resin is treated with a specific compound.

Thus, a production process for a water-absorbing agent, according to the present invention, is characterized by comprising the step of mixing and treating a water-absorbent resin with an oxazoline compound which has at least three structural units of general formula (1) below:

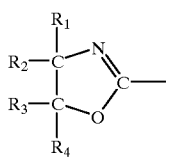

(1)

wherein $R_1 \sim R_4$ separately denote a hydrogen atom, an alkyl group, an aromatic group, a halogen group, a substituted alkyl group, or a substituted aromatic group.

A water-absorbent resin composition, according to the present invention, is characterized by comprising an acidic water-absorbent resin and a basic oxazoline compound.

A crosslinking agent for a water-absorbent resin, according to the present invention, is characterized by comprising an aqueous solution or dispersion of a (co)polymer having at least three structural units of general formula (1) below:

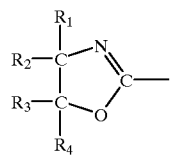

(1)

wherein $R_1 \sim R_4$ separately denote a hydrogen atom, an alkyl group, an aromatic group, a halogen group, a substituted alkyl group, or a substituted aromatic group.

A water-absorbing agent, according to the present invention, is characterized by comprising a water-absorbent resin and an oxazoline compound having at least three structural units of general formula (1) below:

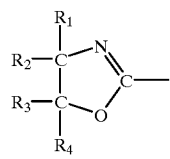

(1)

wherein $R_1 \sim R_4$ separately denote a hydrogen atom, an alkyl group, an aromatic group, a halogen group, a substituted alkyl group, or a substituted aromatic group.

Another water-absorbing agent, according to the present invention, is characterized by having an absorption capacity of not less than 25 (g/g) under a load and a blocking ratio of not higher than 20 weight % under a load.

Another water-absorbing agent, according to the present invention, is characterized by being a product by a crosslinking treatment with an oxazoline compound and having an absorption capacity of not less than 30 (g/g) under no load and an absorption capacity of not less than 25 (g/g) under a load.

An application to a sanitary material, according to the present invention, is characterized by using any one of the above water-absorbing agents according to the present invention.

These and other objects and the advantages of the present invention will be more fully apparent from the following detailed disclosure.

DETAILED DESCRIPTION OF THE INVENTION

Hereinafter, the present invention is explained in detail.

The water-absorbent resin, which is used to produce the water-absorbing agent according to the present invention, is a conventionally known resin that absorbs as large a quantity of water as 50~1,000 times the original in ion-exchanged water under no load to thereby form a hydrogel. Particularly, those which have a carboxyl group are preferable. Typically, the water-absorbent resin is obtainable by polymerizing and crosslinking hydrophilic monomers of which the main component is either one or both of acrylic acid and a salt (neutralized product) thereof. In addition, as to the above water-absorbent resin, those which have an uncrosslinked water-soluble content of not higher than 25 weight %, preferably not higher than 15 weight %, more preferably not higher than 10 weight %, are used.

Examples of the above water-absorbent resins include: crosslinked products of polyacrylic acids (or salts thereof);

hydrolyzed products of starch-acrylonitrile grafted polymers; neutralized products of starch-acrylic acid grafted polymers; saponified products of vinyl acetate-acrylic acid ester copolymers; hydrolyzed products of acrylonitrile- or acrylamide copolymers, and their crosslinked products; modified products of carboxyl-group-containing crosslinked polyvinyl alcohol; crosslinked products of isobutylene-maleic anhydride copolymers; and crosslinked products of cationic polymers such as polyethylenimine and polyallylamine. Among them, the crosslinked products of polyacrylic acids (or salts thereof) are preferably used, wherein examples of the salts include alkaline metal salts, ammonium salts, and amine salts of acrylic acid. It is preferable that the constituent units of the above water-absorbent resin comprise acrylic acid of 10~100 mol % and its salt of 90~0 mol %, more preferably, acrylic acid of 30~100 mol % and its salt of 70~0 mol %, still more preferably, acrylic acid of 32~60 mol % and its salt of 68~40 mol %, wherein the total of both is 100 mol %. Incidentally, this ratio is referred to as neutralization ratio. The monomers, as used to produce the water-absorbent resin by polymerizing hydrophilic monomers (of which the main component is either one or both of acrylic acid and a salt thereof), may, if necessary, comprise not only acrylic acid or a salt thereof, but also monomers other than acrylic acid.

The monomers other than acrylic acid (and its salts) are not especially limited, but specified examples of them include: anionic unsaturated monomers, such as methacrylic acid, maleic acid, vinylsulfonic acid, styrenesulfonic acid, 2-(meth)acrylamido-2-methylpropanesulfonic acid, 2-(meth)acryloylethanesulfonic acid, and 2-(meth)acryloylpropanesulfonic acid, and their salts; nonionic unsaturated monomers containing a hydrophilic group, such as acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloylpiperidine, and N-acryloylpyrrolidine; cationic unsaturated monomers such as N,N-dimethylaminoethyl (meth)acrylate, N,N-diethylaminoethyl (meth)acrylate, N,N-dimethylaminopropyl (meth)acrylate, N,N-dimethylaminopropyl(meth)acrylamide, and their quaternary salts. These monomers may be used either alone respectively or in combinations with each other.

In the present invention, when the monomers other than acrylic acid (and its salts) are used, the ratio of them is preferably not higher than 30 mol %, more preferably not higher than 10 mol %, of the total with acrylic acid and its salts which are used as the main components. If the above monomers other than acrylic acid (and its salts) are used in the above ratio, then the water absorption properties of the resultant water-absorbent resin are still more improved, and the water-absorbent resin is obtainable at a still lower cost.

It is preferable that the water-absorbent resin, as used in the present invention, is acidic in physiological saline in order to achieve the predetermined properties (particularly, absorption capacity and blocking ratio both under a load). This preferable water-absorbent resin, which is acidic, has an acid group as a functional group of a polymer, and is acidic with a pH of preferably not higher than 6.5, more preferably not higher than 6.0, in physiological saline. Preferable examples of the acid group include a carboxyl group, a sulfonic acid group, a sulfinic acid group, and a phosphoric acid group. Incidentally, hereinafter, the water-absorbent resin that is acidic with a pH of not higher than 6.5 might fitly and simply be referred to as "acidic water-absorbent resin." Although there is dependency on the type or molar ratio of the monomer as used, the production of the acidic water-absorbent resin with a pH of not higher than 6.5 requires that, in a process to obtain the water-absorbent resin by polymerizing an acid-group-containing monomer, the pH of the resulting water-absorbent resin should be adjusted so as to fall in the acid region of not higher than 6.5 by no neutralization of the acid-group-containing monomer before or during the polymerization or no neutralization of the resulting polymer, or by neutralization in a low ratio, as it were, low neutralization, of the acid group.

As to the water-absorbent resin as used in the present invention, it is preferable for achievement of the predetermined properties that the pH of the resin is in the acid region. Especially, water-absorbent resins of which the pH is preferably not higher than 6.0, more preferably in the range of 6.0 to 4.0, still more preferably 5.9 to 4.2, particularly preferably 5.8 to 4.8, are used. The type or pH of the monomer as used for polymerization to obtain the water-absorbent resin, and further, additives, may be adjusted so that the pH of the resin will be kept in such a range.

When the above hydrophilic monomer (of which the main component is acrylic acid or a salt thereof) is, for example, polymerized to obtain the water-absorbent resin as used in the present invention, bulk polymerization or precipitation polymerization can be carried out. However, considering the performance or the easiness of the polymerization control, it is preferable to carry out aqueous solution polymerization or reversed-phase suspension polymerization using the above hydrophilic monomer in the form of its aqueous solution. Incidentally, when the monomer is used in the form of its aqueous solution, the concentration of the monomer in its aqueous solution (hereinafter referred to as "aqueous monomer solution") is not especially limited, but is preferably in the range of 10~70 weight %, more preferably 20~40 weight %. In addition, when the above aqueous solution polymerization or reversed-phase suspension polymerization is carried out, a solvent other than water may be jointly used if necessary, and the kind of the solvent as jointly used is not especially limited.

When the above polymerization is initiated, the following radical polymerization initiators, for example, can be used: potassium persulfate, ammonium persulfate, sodium persulfate, t-butyl hydroperoxide, hydrogen peroxide, and 2,2'-azobis(2-amidinopropane) dihydrochloride.

Furthermore, a redox initiator is also available by further using a reductant to promote decomposition of the above polymerization initiator and combining both with each other. Examples of the above reductant include: (bi)sulfurous acid (or its salts) such as sodium sulfite and sodium hydrogensulfite; L-ascorbic acid (or its salts); reducible metals (or their salts) such as ferrous salts; and amines. However, the reductant is not especially limited to them.

The amount of the above polymerization initiator as used is in the range of usually 0.001~2 mol %, preferably 0.01~0.1 mol %. In the case where the amount of the polymerization initiator is smaller than 0.001 mol %, there are disadvantages in that a large amount of monomers remain unreacted, so the amount of monomers, remaining in the resultant water-absorbent resin, increases. On the other hand, in the case where the amount of the polymerization initiator exceeds 2 mol %, there might be disadvantages in that the water-soluble content in the resultant water-absorbent resin increases.

In addition, the polymerization reaction may be initiated by irradiating the reaction system with active energy rays, such as radiations, electron beam, and ultraviolet rays, instead of using the polymerization initiators. Incidentally, the reaction temperature in the above polymerization reaction is not especially limited, but is preferably in the range of 20~90° C. In addition, the reaction time is not especially limited either and may fitly be set according to factors such as the respective kinds of the hydrophilic monomers and polymerization initiators and the reaction temperature.

The water-absorbent resin, used in the present invention, may be a self-crosslinking type using no crosslinking agent, but preferable ones are those which are copolymerized or reacted with an internal-crosslinking agent having at least two polymerizable unsaturated groups or reactive groups per molecule.

Specified examples of the above internal-crosslinking agent include: N,N-methylenebis(meth)acrylamide, (poly)ethylene glycol di(meth)acrylate, (poly)propylene glycol di(meth)acrylate, trimethylolpropane tri(meth)acrylate, glycerol tri(meth)acrylate, glycerol acrylate methacrylate, ethylene-oxide-modified trimethylolpropane tri(meth)acrylate, pentaerythritol hexa(meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, propylene glycol, glycerol, pentaerythritol, ethylenediamine, ethylene carbonate, propylene carbonate, polyethylenimine, and glycidyl (meth)acrylate.

These internal-crosslinking agents may be used either alone respectively or in combinations with each other. In addition, these internal-crosslinking agents may be added to the reaction system either all at once or divisionally. When these internal-crosslinking agents are used, it is preferable to essentially use a compound with at least two polymerizable unsaturated groups, considering the water absorption properties of the resultant water-absorbent resin.

The amount of the above internal-crosslinking agent as used is in the range of preferably 0.005~2 mol %, more preferably 0.01~1 mol %, still more preferably 0.03~0.5 mol %, most preferably 0.06~0.3 mol %, of the above hydrophilic monomers. In the respective cases where the amount of the internal-crosslinking agent is smaller than 0.005 mol % and where the amount of the internal-crosslinking agent exceeds 2 mol %, the water-absorbent resin having the desired water absorption properties might not be obtained.

When the crosslinking structure is introduced into the internal portion of the water-absorbent resin using the above internal-crosslinking agent, the internal-crosslinking agent may be added to the reaction system during or after polymerization, or after polymerization and neutralization, of the above hydrophilic monomers.

Incidentally, in the above polymerization, the following materials may be added to the reaction system: various foaming agents such as carbonates (or hydrogencarbonates), carbon dioxide, azo compounds, and inert organic solvents; hydrophilic polymers such as starch, cellulose, their derivatives, polyvinyl alcohol, polyacrylic acid (or its salts), and crosslinked products of polyacrylic acid (or its salts); various surface-active agents; and chain transfer agents such as hypophosphorous acid (or its salts).

When the water-absorbent resin as obtained by the above polymerization reaction is a gel, the above water-absorbent resin is usually dried and, if necessary, pulverized.

The water content of the water-absorbent resin, usable in the present invention, is not especially limited, but is in the range of usually about 1~about 400 weight %, preferably 1~40 weight % (but not including 40 weight %), more preferably 1~10 weight %. The oxazoline compound, as used in the present invention, has a controlled permeability into the water-absorbent resin, therefore, enables even the surface-crosslinking, as has ever been difficult, of a water-absorbent resin having a high water content.

In addition, the particle size in diameter of the water-absorbent resin, usable in the present invention, may exceed 1,000 μm in terms of average particle size in diameter of a gel that is obtained by the polymerization reaction and has not been dried or pulverized yet. However, the particle size in diameter is usually in the range of 10~1,000 μm, preferably 50~800 μm, more preferably 75~600 μm (but not including 75 μm), particularly preferably 150~600 μm (but not including 150 μm), most preferably 200~600 μm, on the average. Furthermore, the ratio of fine powder particles (for example, having a particle size of not greater than 150 μm in diameter) in the water-absorbent resin is preferably as low as possible, specifically, not higher than 10 weight %, more preferably not higher than 5 weight %, particularly preferably not higher than 1 weight %. The particle shape of the water-absorbent resin as obtained in this way, for example, may be spherical, pulverized, or irregular, and is not especially limited, but those which have the irregular pulverized shapes, as obtained via the pulverization step, are preferably used.

Among the water-absorbent resins as obtained by the above method, it is preferable to use those which display a high value of saturated absorption capacity of not less than 40 g/g, preferably not less than 45 g/g, for physiological saline under no load, because the effects of the present invention are remarkably shown by such a resin. Of course, the above absorption capacity is fitly adjusted according to the purpose.

The present invention can be achieved by the process comprising the step of mixing and treating a water-absorbent resin with a specific oxazoline compound, wherein the water-absorbent resin is obtainable by the above polymerization.

The oxazoline compounds, usable in the present invention, have at least three structural units of general formula (1) below:

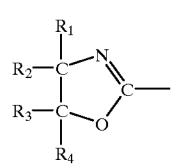

(1)

wherein $R_1$~$R_4$ separately denote a hydrogen atom, an alkyl group, an aromatic group, a halogen group, a substituted alkyl group, or a substituted aromatic group.

These oxazoline compounds are, preferably, water-soluble ones, more preferably, polymers. These preferably usable oxazoline-group-containing polymers can be obtained by polymerizing an addition-polymerizable oxazoline (a) and at least one other monomer (b) as is used if necessary. Addition-polymerizable oxazoline (a) is shown by general formula (2) below:

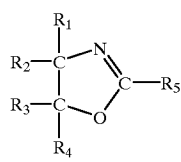

(2)

wherein: $R_1$~$R_4$ separately denote a hydrogen atom, an alkyl group, an aromatic group, a halogen group, a substituted alkyl group, or a substituted aromatic group, and $R_5$ denotes an acyclic organic group having an addition-polymerizable unsaturated bond.

Specific examples of addition-polymerizable oxazoline (a) include 2-vinyl-2-oxazoline, 2-vinyl-4-methyl-2-oxazoline, 2-vinyl-5-methyl-2-oxazoline, 2-isopropenyl-2-oxazoline, 2-isopropenyl-4-methyl-2-oxazoline, and 2-isopropenyl-5-ethyl-2-oxazoline. At least one member selected from the group consisting of these compounds is usable. Among them, 2-isopropenyl-2-oxazoline is preferable.

The amount of addition-polymerizable oxazoline (a) as used is not especially limited, but is preferably not smaller than 5 weight %, more preferably not smaller than 10 weight %, particularly preferably not smaller than 20 weight %, of the monomer mixture as used to obtain the oxazoline-group-containing polymer. In the case where the amount is smaller than 5 weight %, effects of reforming the water-absorbent resin might be so inferior that no water-absorbing agent having excellent absorption capacity under a load could be obtained.

At least one other monomer (b), as used if necessary to obtain the oxazoline-group-containing polymer which is preferably used as the oxazoline compound in the present invention, is not especially limited if it is a monomer that is unreactable with the oxazoline group and copolymerizable with addition-polymerizable oxazoline (a). Examples thereof include: (meth)acrylate esters such as methyl (meth) acrylate, butyl (meth)acrylate, 2-ethylhexyl (meth)acrylate, methoxypolyethylene glycol (meth)acrylate, 2-hydroxyethyl (meth)acrylate, and 2-aminoethyl (meth) acrylate and its salts; (meth)acrylate salts such as sodium (meth)acrylate and ammonium (meth)acrylate; unsaturated nitriles such as (meth)acrylonitrile; unsaturated amides such as (meth)acrylamide, N-methylol(meth)acrylamide, and N-(2-hydroxyethyl)(meth)acrylamide; vinyl esters such as vinyl acetate and vinyl propionate; vinyl ethers such as methyl vinyl ether and ethyl vinyl ether; α-olefins such as ethylene and propylene; halogen-containing α,β-unsaturated monomers such as vinyl chloride, vinylidene chloride, and vinyl fluoride; and α,β-unsaturated aromatic monomers such as styrene, α-methylstyrene, and sodium styrenesulfonate. These may be used either alone respectively or in combinations with each other.

As is mentioned above, the oxazoline compound in the present invention is preferably a polymer, particularly preferably a copolymer. Especially, for more achieving the object of the present invention, it is preferable that the oxazoline compound is a copolymer as obtained by polymerizing a monomer mixture that includes the above addition-polymerizable oxazoline and a (meth)acrylate ester, particularly, an acrylate ester. In the case of the copolymer, the respective amounts of the addition-polymerizable oxazoline and the (meth)acrylate ester are as follows: relative to the total of all monomers, including other monomers (if necessary), as used to obtain the copolymer, the amount of the addition-polymerizable oxazoline is preferably not smaller than 5 weight %, more preferably in the range of 5 to 95 weight %, still more preferably 20 to 80 weight %, and the amount of the (meth)acrylate ester is preferably not smaller than 0.25 weight %, more preferably in the range of 5 to 95 weight %.

In addition, the weight-average molecular weight of the oxazoline compound in the present invention is preferably in the range of 1,000 to 1,000,000, more preferably 10,000 to 500,000, particularly preferably 50,000 to 200,000. In the case where the weight-average molecular weight of the oxazoline compound is lower than 1,000, the permeability of the oxazoline compound into the water-absorbent resin might be so high that it might be difficult to form an adequate surface-crosslinked layer, and further that the safety or the surface treatment effects might be low. In the case where the weight-average molecular weight of the oxazoline compound is higher than 1,000,000, the permeability of the oxazoline compound into the water-absorbent resin might be so low that it might be difficult to form an adequate surface-crosslinked layer.

The oxazoline-group-containing polymer, which is preferably used as the oxazoline compound in the present invention, generally can be produced by polymerizing a monomer mixture including addition-polymerizable oxazoline (a) and at least one other monomer (b), as is used if necessary, by conventional polymerization methods such as solution polymerization in an aqueous medium. The aqueous medium is not especially limited it is miscible with water, but examples thereof include water and a mixed solution of water and a hydrophilic solvent, wherein examples of the hydrophilic solvent include: lower alcohols such as methyl alcohol, ethyl alcohol, n-propyl alcohol, isopropyl alcohol, n-butyl alcohol, isobutyl alcohol, and t-butyl alcohol; ketones such as acetone and methyl ethyl ketone; ethers such as dioxane, tetrahydrofuran, and methoxy(poly)ethylene glycol; amides such as ε-caprolactam and N,N-dimethylformamide; sulfoxides such as dimethyl sulfoxide; polyhydric alcohols and their derivatives, such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymer, pentaerythritol, sorbitol, ethylene glycol monomethyl ether, and ethylene glycol monobutyl ether. These may be used either alone respectively or in combinations with each other.

The oxazoline-group-containing polymer, usable in the present invention, may be produced by other than the above processes. Examples thereof include: a process in which the oxazoline-group-containing polymer is synthesized using a nitrile-group-containing polymer as a raw material (refer to JP-A-09-235320); and a process in which the oxazoline-group-containing polymer is synthesized from a poly(meth) acrylate ester (refer to U.S. Pat. No. 5,705,573). As a matter of course, other than these processes may be used.

The oxazoline compound, usable in the present invention, may be a hydrophobic or water-dispersible one, but is preferably a water-soluble one. Water-soluble oxazoline compounds, which have a solubility of preferably not lower than 1 g, more preferably not lower than 10 g, particularly preferably not lower than 50 g, to 100 g of water at room temperature, are usable. In the case of the oxazoline-group-containing polymer which is preferably used, the concentration of hydrophilic, particularly, water-soluble, monomers in the monomer mixture is usually not lower than 50 weight %, preferably not lower than 70 weight %. Examples of the hydrophilic monomer, as referred to herein, include addition-polymerizable oxazoline (a). Examples of the at least one other monomer (b), as used if necessary, include methoxypolyethylene glycol (meth)acrylate, 2-hydroxyethyl (meth)acrylate, and 2-aminoethyl (meth) acrylate and its salts, and further, (meth)acrylate salts (e.g. sodium (meth)acrylate, ammonium (meth)acrylate), (meth) acrylonitrile, (meth)acrylamide, N-methylol(meth) acrylamide, N-(2-hydroxyethyl)(meth)acrylamide, and sodium styrenesulfonate.

The oxazoline compound, which is to be mixed with the water-absorbent resin in the present invention, is preferably basic, and further, preferably more basic than the water-absorbent resin. Especially, the pH of the oxazoline compound in water is preferably in the range of 7 to 14, more preferably 7 to 9, particularly preferably 8 to 9. In addition, the difference in pH between the oxazoline compound and the water-absorbent resin is preferably not less than 1, more preferably not less than 2, particularly preferably in the range of 2 to 7, and it is preferable that the oxazoline compound is basic. Such a water-absorbent resin composition, comprising the acidic water-absorbent resin and the basic oxazoline compound, is the most preferable for achieving the present invention. In the case where the pH of the oxazoline compound as used deviates from these ranges, the aimed properties are not achieved. In addition, the oxazoline compound, which is used as the crosslinking agent in the present invention, is preferably in the form of an aqueous solution or dispersion, more preferably an aqueous solution. To regulate the pH so as to be in the above-aimed range, a pH-adjusting agent may be added if necessary or preferably. Examples of usable pH-adjusting agents include volatile amines, ammonia, and organic amines. Incidentally, the pH of the oxazoline compound in ion-exchanged water is measured in the form of an aqueous solution thereof with a concentration of about 10 to about 40 weight %. In addition, the pH of the oxazoline compound in ion-exchanged water is fitly adjusted by adjusting not only the composition of the monomers, but also polymerization initiators (or pH thereof) or additives (or pH thereof).

Unlike the epoxy group, the oxazoline compound as used in the present invention has no property to stimulate skin and is therefore excellent in the safety as well. In addition, the oxazoline compound further has relatively high reactivity with the water-absorbent resin and can rapidly form the crosslinking structure. Therefore, the above crosslinking agents, usable in the present invention, does not deteriorate inner or other portions of the water-absorbent resin and therefore does not lower the water absorption properties. Thus, the water-absorbing agent according to the present invention is excellent in both the absorption capacities under no load and under a load, and can exhibit under a load a blocking ratio as largely improved by that the oxazoline compound reforms the surface of the water-absorbent resin. Particularly, in the case where the above polymer is used, the oxazoline compound forms a hardened film on the surface of the water-absorbent resin, thereby exhibiting great effects upon the impact resistance (effects to inhibit the deterioration of dry properties, for example, during the transportation of powders) and hygroscopic fluidity resistance of the resulting water-absorbing agent.

In addition, in the present invention, the oxazoline compound is preferably usable not only as a crosslinking agent for the surface portion of the water-absorbent resin, but also as the above internal-crosslinking agent.

The water-absorbing agent according to the present invention is obtainable by the process comprising the step of mixing and treating the above water-absorbent resin with the above oxazoline compound.

The amount of the oxazoline compound, as used in this process, is preferably in the range of about 0.001~about 10 weight parts, more preferably about 0.01~about 5 weight parts, particularly preferably about 0.05~about 3 weight parts, per 100 weight parts of the water-absorbent resin. Amounts exceeding 10 weight parts are unfavorable, not only because they are uneconomical, but also because they are excessive to the formation of the optimum crosslinking structure in the water-absorbing agent. Furthermore, amounts smaller than 0.001 weight parts might result in little width of improving the properties of the water-absorbing agent such as absorption capacity and blocking ratio both under a load.

It is preferable to use water when the water-absorbent resin is mixed with the oxazoline compound in the present invention. The amount of water, as used, is different according to factors such as the kind, particle size in diameter, or water content of the water-absorbent resin, but is in the range of preferably 0~20 weight parts (but not including zero), more preferably 0.5~20 weight parts, still more preferably 0.5~10 weight parts.

In addition, in the present invention, when the water-absorbent resin is mixed with the oxazoline compound or its aqueous solution, hydrophilic organic solvents (as the solvent) or third substances may be used to raise the miscibility and the reactivity.

When the hydrophilic organic solvent is used, examples thereof include: lower alcohols such as methyl alcohol, ethyl alcohol, n-propyl alcohol, isopropyl alcohol, n-butyl alcohol, isobutyl alcohol, and t-butyl alcohol; ketones such as acetone and methyl ethyl ketone; ethers such as dioxane, tetrahydrofuran, and methoxy(poly)ethylene glycol; amides such as ε-caprolactam and N,N-dimethylformamide; sulfoxides such as dimethyl sulfoxide; polyhydric alcohols and their derivatives, such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymer, pentaerythritol, sorbitol, ethylene glycol monomethyl ether, and ethylene glycol monobutyl ether.

The amount of the hydrophilic organic solvent as used is different according to factors such as the kind, particle size in diameter, or water content of the water-absorbent resin, but is preferably not larger than 20 weight parts, more preferably in the range of 0.1~10 weight parts, per 100 weight parts of the solid content of the water-absorbent resin.

Furthermore, surfactants or inert inorganic fine powders may be used as third substances other than the crosslinking agent and the solvent in order to enhance the miscibility and the properties. The surfactants or inert inorganic fine powders as used are exemplified in documents such as U.S. Pat. No. 5,164,459, EP 827753, EP 349240, and EP 761241.

In addition, it is preferable that not only the aforementioned materials such as surfactants or inert inorganic fine powders, but also materials as disclosed in EP 0668080, such as inorganic acids, organic acids, or polyamino acids, are let to coexist as the third substances, because the reaction of the oxazoline might thereby be further accelerated to greatly enhance effects of reforming the properties such as absorption capacity under a load. Examples of the inorganic or organic acid include sulfuric acid, phosphoric acid, hydrochloric acid, citric acid, glyoxylic acid, glycolic acid, glycerol phosphate, glutaric acid, cinnamic acid, succinic acid, acetic acid, tartaric acid, lactic acid, pyruvic acid, fumaric acid, propionic acid, 3-hydroxypropionic acid, malonic acid, butyric acid, isobutyric acid, imidinoacetic acid, malic acid, isethionic acid, citraconic acid, adipic acid, itaconic acid, crotonic acid, oxalic acid, salicylic acid, gallic acid, sorbic acid, p-toluenesulfonic acid, and gluconic acid. Although there is dependency on the pH of the water-absorbent resin as used, the surface-crosslinking with the oxazoline compound in the present invention prefers to further use the above acid compound. The amount of the acid compound as used is preferably in the range of 0 to 10 weight %, more preferably 0.1 to 5 weight %, of the water-absorbent resin.

In addition, conventional surface-crosslinking agents may further be used if they do not hinder the effects of the present invention. Examples of the conventional surface-crosslinking agents include: polyhydric alcohol compounds such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymer, pentaerythritol and sorbitol; epoxy compounds such as ethylene glycol diglycidyl ether, polyethylene diglycidyl ether, glycerol polyglycidyl ether, diglycerol polyglycidyl ether, polyglycerol polyglycidyl ether, propylene glycol diglycidyl ether, polypropylene glycol diglycidyl ether and glycidol; polyamine compounds, such as ethylenediamine, diethylenetriamine, triethylenetetramine, tetraethylenepentamine, pentaethylenehexamine and polyethylenimine, and their inorganic or organic salts (for example, azetidinium salts); polyisocyanate compounds such as 2,4-tolylene diisocyanate and hexamethylene diisocyanate; polyoxazoline compounds such as 1,2-ethylenebisoxazoline; alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxopan-2-one; haloepoxy compounds, such as epichlorohydrin, epibromohydrin and α-methylepichlorohydrin, and their polyamine adducts (for example, Kymene made by Hercules: registered trademark); silane coupling agents such as γ-glycidoxypropyltrimethoxysilane and γ-aminopropyltriethoxysilane; and polyvalent metallic compounds such as hydroxides and chlorides of zinc, calcium, magnesium, aluminum, iron and zirconium; all of which are conventional crosslinking agents.

When the water-absorbent resin is mixed with the oxazoline compound, it is, for example, permissible to mix the oxazoline compound with a dispersion as prepared by dispersing the water-absorbent resin into the above hydrophilic organic solvent. In addition, the solvent, water, the oxazoline compound, or a mixture thereof may be added divisionally into at least two times. However, the mixing method is not especially limited. In a preferable method among various mixing methods, the oxazoline compound (if necessary, in the form of solution with either one or both of water and the hydrophilic organic solvent) is directly sprayed or dropped to the water-absorbent resin, thereby mixing them. In addition, when the mixing is carried out using water, it is permissible that a material such as a water-insoluble finely particulate powder or a surfactant is let to coexist if it does not hinder the effects of the present invention.

It is preferable that the mixing apparatus, as used to mix the water-absorbent resin and the oxazoline compound in the present invention, has a great mixing force to mix both materials uniformly and surely. Preferable examples of the above mixing apparatus include: cylinder type mixers, double-wall cone type mixers, V-character-shaped mixers, ribbon type mixers, screw type mixers, fluidized-furnace rotary disk type mixers, gas current type mixers, double-arm type kneaders, internal mixers, pulverizing type kneaders, rotary mixers, and screw type extruders, and more preferable ones are high-speed agitation type mixers.

The treatment, which is carried out after the water-absorbent resin and the oxazoline compound are mixed, as referred to in the present invention, is, for example, a treatment to run the crosslinking reaction, for which it is generally preferable to carry out a heating treatment. The temperature of the above heating treatment is different according to the type of the oxazoline compound as used, but is preferably in the range of 40~250° C. In the case where the treatment temperature is lower than 40° C., no uniform crosslinking structure might be formed, so that no water-absorbing agent, excellent in the balance between the absorption capacities under no load and under a load, could be obtained. In the case where the treatment temperature exceeds 25° C., the deterioration of the water-absorbent resin might occur to depress the performance of the water-absorbing agent, therefore caution is necessary. The treatment temperature is preferably in the range of 80~220° C., more preferably 100~200° C., particularly preferably 120~190° C.

In addition, when the volatile base is further used above, it is preferable to carry out sufficient heating to thereby volatilize the base as added to the water-absorbent resin.

The above heating treatment can be carried out using conventional dryers or heating-furnaces. Examples of the dryers include: channel type mixing dryers, rotary dryers, disk dryers, fluidized-bed dryers, gas-stream type dryers, and infrared dryers.

The above-mentioned production process according to the present invention can give a water-absorbing agent which is excellent in both absorption capacities under no load and under a load and further in the blocking ratio under a load, and is of good workability and high safety, therefore, displays excellent absorption properties even if the weight percentage of the water-absorbent resin (resin concentration) is high when the water-absorbent resin is used for materials such as sanitary materials.

The water-absorbing agent, resultant from the above process, is a water-absorbing agent which is a product by the crosslinking treatment with the oxazoline compound and has an absorption capacity of not less than 30 (g/g), preferably not less than 35 (g/g), under no load, and further, an absorption capacity of not less than 25 (g/g), preferably not less than 27 (g/g), particularly preferably not less than 28 (g/g), under a load. Such a water-absorbing agent, preferably, has an average particle size of 200 to 600 μm in diameter and contains fine particles with a particle size of not greater than 150 μm in diameter in the ratio of not higher than 10 weight %, and further has a pH of preferably not higher than 6.0, more preferably in the range of 6.0 to 4.0, still more preferably 5.9 to 4.2, particularly preferably 5.8 to 4.2, in physiological saline. Furthermore, this water-absorbing agent has a blocking ratio of not higher than 20 weight %, preferably not higher than 10 weight %, and particularly preferably, substantially 0 weight %, under a load.

In addition, the present invention further provides a water-absorbing agent which has an absorption capacity of not less than 25 (g/g), preferably not less than 27 (g/g), particularly preferably not less than 28 (g/g), under a load, and further, a blocking ratio of not higher than 20 weight %, preferably not higher than 10 weight %, and particularly preferably, substantially 0 weight %, under a load.

In addition, the present invention further provides a sanitary material comprising any of the above water-absorbing agents according to the present invention.

When used for sanitary materials such as disposable diapers, the water-absorbing agent according to the present invention is used for absorbent structures that preferably have a high resin concentration of 30 to 100 weight %, more preferably 40 to 90 weight %, particularly preferably 50 to 80 weight %. In addition, the absorbent core of the absorbent structure is subjected to compression forming so as to have a density of 0.06~0.5 g/cc and a basis weight of 0.01~0.20 g/cm$^2$. Incidentally, the fibrous material as used is preferably in the form of air-laid pad of a hydrophilic fiber, such as pulverized wood pulp, and further, other examples can include cotton linters, crosslinked cellulose fibers, rayon, cotton, wool, acetate, and vinylon. The water-absorbing agent according to the present invention is excellent in the absorption capacity under a load, the blocking property under a load, and the safety, and further in the hygroscopic fluidity even if no inorganic fine powder that has bad effects on the miscibility with the fiber is used. Therefore, an absorbent structure in which the fiber and the resin are uniformly blended with good workability is producible even in the case where the resin concentration is high such that the weight ratio of the water-absorbent resin to the total of the water-absorbing agent and the fibrous material is not lower than 30 weight %.

In addition, in the present invention, various functions also can be given to the above water-absorbing agents by further adding thereto materials such as disinfectants, deodorants, antimicrobial agents, perfumes, various inorganic powders, foaming agents, pigments, dyes, hydrophilic short fibers, manure, oxidants, reductants, water, and salts.

Furthermore, as is mentioned above, the above water-absorbing agent can particularly favorably be used for various absorbent articles, particularly, absorbent structures as are getting thinned more and more, such as disposable diapers, sanitary napkins, and incontinent pads. (Effects and Advantages of the Invention):

The production process according to the present invention can give a resin by a simple process using a treating agent of high safety, wherein the resin is excellent in the absorption capacities under no load and under a load and in the blocking ratio under a load. The water-absorbing agent according to the present invention can display excellent absorption properties even if the weight percentage of the water-absorbent resin (resin concentration) is high when the water-absorbent resin is used for materials such as sanitary materials.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to these examples. Incidentally, in the examples, unless otherwise noted, the unit "part(s)" is by weight.

<Performances of Water-absorbing Agent>

They were measured by the following methods:

(a) Absorption capacity under no load:

First, 0.2 g of water-absorbent resin (water-absorbing agent) was uniformly placed into a nonwoven-fabric-made bag (60 mm×60 mm) and then immersed into a 0.9 wt % aqueous sodium chloride solution (physiological saline). Sixty minutes later, the bag was drawn up and then drained at 250 G for 3 minutes with a centrifuge, and the resultant weight W1 (g) of the bag was then measured. On the other hand, the same procedure was carried out using no water-absorbing agent, and the resultant weight W0 (g) was measured. Thus, the absorption capacity (g/g) under no load was calculated from these weights W1 and W0 in accordance with the following equation:

absorption capacity (g/g) under no load=(weight W1 (g)−weight W0 (g))/(weight (g) of water-absorbing agent).

(b) Absorption capacity under load:

First, 0.9 g of water-absorbent resin (water-absorbing agent) is uniformly spread on a stainless wire gauze of 400 mesh (mesh opening size: 38 μm) as attached by fusion to the bottom of a plastic supporting cylinder of inner diameter 60 mm, on which a piston and a load are further mounted in sequence, wherein the piston has an outer diameter only a little smaller than 60 mm and makes no gap with the wall face of the supporting cylinder, but is not hindered from moving up and down, and the total weight of the piston and the load are adjusted to about 565 g to uniformly apply a load of 20 g/cm$^2$ (1,961 Pa) to the water-absorbing agent. Then, the weight (Wa) of the resultant set of measurement apparatus is measured.

A glass filter of 90 mm in diameter is mounted inside a Petri dish of 150 mm in diameter, and a 0.9 weight % aqueous NaCl solution is added up to the same level as the surface of the glass filter, on which GF/A filter paper of 9 cm in diameter for glass filters is then mounted such that its entire surface will be wetted, and the excessive liquid is removed.

The above set of measurement apparatus is mounted on the above wet filter paper for glass filters, thereby allowing the water-absorbing agent to absorb the liquid under a load. After 1 hour, the set of measurement apparatus is removed by lifting it, and its weight (Wb) is measured again. The absorption capacity under a load is determinable in accordance with the following equation:

Absorption capacity (g/g) under load=(Wb−Wa)/0.9

(c) Blocking ratio under load:

First, 5 g of water-absorbing agent (or water-absorbent resin) is uniformly spread on the bottom of a polypropylene cup of 60 mm in bottom diameter. Immediately thereafter, this cup is put into a thermo-humidistat as adjusted beforehand to 25° C. and relative humidity 80%, and then left for 1 hour. Then, after being provided with a load of 1.0 psi (6.89×10$^3$ Pa) for 1 minute, the water-absorbing agent is caused to pass through a JIS standard sieve of 7.5 cm in diameter and 2,000 μm (ASTM No. 10 mesh) in mesh opening size according to JIS. After slightly vibrating the sieve, measurement is made with regard to the weight (W1) of block-shaped water-absorbing agent portions which have not passed through the sieve, but remains on the gauze, and the weight (W0) of water-absorbing agent portions which have passed through the sieve. The blocking ratio under a load is calculated in accordance with the equation below. What is lower in this value has a tendency to less cause blocking even if a pressure is applied to the humidified resin.

Blocking ratio under load (%)=W1/(W1+W0)×100

(d) pH of water-absorbent resin/pH of crosslinking agent:

An amount of 1.0 g of water-absorbent resin was dispersed into 100 g of physiological saline (temperature= 23±2° C.), and the resultant mixture was stirred with a stirrer for 30 minutes, and then the pH of the resultant swollen-gel dispersion was measured. Incidentally, the pH was measured with a pH meter (glass electrode hydrogen ion concentration meter, made by Horiba Seisakusho Co., Ltd.).

Referential Example 1

A reaction solution was prepared by dissolving 4.0 weight parts of polyethylene glycol diacrylate (n=8) (as the internal-crosslinking agent) into 5,500 parts of a 33 weight % aqueous solution of partially neutralized acrylic acid (neutralization ratio: 60 mol %) (as the monomer component). Next, this reaction solution was degassed under a nitrogen gas atmosphere for 30 minutes.

Then, the reaction solution was supplied into a reaction vessel as prepared by capping a stainless-steel-made double-arm type kneader having two sigma type vanes and a jacket. While maintaining the reaction solution at 30° C., internal air of the above reaction vessel was replaced with nitrogen gas. Next, while the reaction solution was stirred, 2.4 parts of ammonium persulfate (as the polymerization initiator) and 0.12 parts of L-ascorbic acid (as the reductant to promote the decomposition of the polymerization initiator) were added to the reaction solution, so that a polymerization reaction got started about 1 minute after. The polymerization was carried out at 30–80° C., and the resultant hydrogel polymer as small divided into the particle size of about 1 mm in diameter was got out 60 minutes after the initiation of the polymerization.

The resultant hydrogel polymer was spread on a wire gauze of 300 μm in mesh opening size and then dried at 150° C. with hot air for 90 minutes. Then, the resultant dried product was pulverized with a vibration mill and then further classified with JIS standard wire gauzes of 500 μm and 150 μm respectively in mesh opening size, thus obtaining water-absorbent resin (1) as pulverized into the irregular shape with an average particle size of 370 μm in diameter, in which the ratio of the particles having a particle size smaller than 150 μm in diameter was 0.5 weight %. The pH of water-absorbent resin (1) was about 5.7.

Referential Example 2

Water-absorbent resin (2), as pulverized into the irregular shape with an average particle size of 400 μm in diameter, in which the ratio of the particles having a particle size smaller than 150 μm in diameter was 1.0 weight %, was obtained in the same way as of Referential Example 1 except that partially neutralized acrylic acid having a neutralization ratio of 75 mol % was used as the monomer component. The pH of water-absorbent resin (2) was about 6.1.

Referential Example 3

Water-absorbent resin (3), as pulverized into the irregular shape with an average particle size of 400 μm in diameter, in which the ratio of the particles having a particle size smaller than 150 μm in diameter was 1.0 weight %, was obtained in the same way as of Referential Example 1 except that 5,500 parts of an aqueous solution of partially neutralized acrylic acid having a neutralization ratio of 60 mol % and a concentration of 37 weight % was used as the monomer component. The pH of water-absorbent resin (3) was about 5.5.

Example 1

One hundred weight parts of water-absorbent resin (1), as obtained in Referential Example 1, was mixed with an aqueous treating agent solution comprising 0.8 weight parts of oxazoline compound, 20 weight parts of water, and 8 weight parts of isopropanol, wherein the oxazoline compound was a copolymer comprising (2-isopropenyl-2-oxazoline)/(ethyl acrylate)/(ethyl methacrylate)/(monomethoxypolyethylene glycol acrylate)=50/2/28/20 weight % (pH=8~9 as aqueous solution; weight-average molecular weight=about 70,000). The resultant mixture was heated at 185° C. for 60 minutes to obtain water-absorbing agent (1), of which the absorption capacity under no load, the absorption capacity under a load. and the blocking ratio under a load were 31 (g/g), 27 (g/g), and 0% respectively as shown in Table 1.

Example 2

One hundred weight parts of water-absorbent resin (1), as obtained in Referential Example 1, was mixed with an aqueous treating agent solution comprising 0.8 weight parts of oxazoline compound, 10 weight parts of water, and 8 weight parts of isopropanol, wherein the oxazoline compound was a copolymer comprising (2-isopropenyl-2-oxazoline)/(ethyl acrylate)/(ethyl methacrylate)/(monomethoxypolyethylene glycol acrylate)=50/2/28/20 weight % (pH=8~9 as aqueous solution; weight-average molecular weight=about 70,000). The resultant mixture was heated at 185° C. for 60 minutes to obtain water-absorbing agent (2), of which the absorption capacity under no load, the absorption capacity under a load. and the blocking ratio under a load were 36 (g/g), 28 (g/g), and 0% respectively as shown in Table 1.

Example 3

One hundred weight parts of water-absorbent resin (2), as obtained in Referential Example 2, was mixed with an aqueous treating agent solution comprising 10 weight parts of sulfuric acid, 2 weight parts of oxazoline compound, 8 weight parts of water, and 8 weight parts of isopropanol, wherein the oxazoline compound was a copolymer comprising (2-isopropenyl-2-oxazoline)/(ethyl acrylate)/(ethyl methacrylate)/(monomethoxypolyethylene glycol acrylate)= 50/2/28/20 weight % (pH=8~9 as aqueous solution; weight-average molecular weight=about 70,000). The resultant mixture was heated at 180° C. for 60 minutes to obtain water-absorbing agent (3), of which the absorption capacity under no load, the absorption capacity under a load. and the blocking ratio under a load were 36 (g/g), 26 (g/g), and 0% respectively as shown in Table 1.

Example 4

Water-absorbing agent (4), of which the absorption capacity under no load, the absorption capacity under a load. and the blocking ratio under a load were 37 (g/g), 25 (g/g), and 0% respectively as shown in Table 1, was obtained in the same way as of Example 3 except that no sulfuric acid was used. From this result, it was found that no use of sulfuric acid, namely, high pH of the water-absorbent resin, would result in somewhat low absorption capacity under a load.

Example 5

Water-absorbent resin (2), as obtained in Referential Example 2, was classified into a fraction having a particle size of 300 to 600 μm in diameter, and then a mixed solution comprising 0.8 weight parts of oxazoline compound, 10 weight parts of water, and 8 weight parts of isopropanol was added to 100 weight parts of the above fraction, wherein the oxazoline compound was a copolymer comprising (2-isopropenyl-2-oxazoline)/(ethyl acrylate)/(ethyl methacrylate)=85/5/10 weight % (pH=8~9 as aqueous solution; weight-average molecular weight=about 100,000). The resultant mixture was heated at 185° C. for 60 minutes to obtain water-absorbing agent (5), of which the absorption capacity under no load, the absorption capacity under a load. and the blocking ratio under a load were 43 (g/g), 25 (g/g), and 33% respectively as shown in Table 1.

Example 6

Water-absorbing agent (6), of which the absorption capacity under no load, the absorption capacity under a load. and the blocking ratio under a load were 44 (g/g), 21 (g/g), and 83% respectively as shown in Table 1, was obtained in the same way as of Example 5 except that 0.8 weight parts of oxazoline copolymer was replaced with 0.8 weight parts of polyisopropenyloxazoline (weight-average molecular weight=about 50,000). Thus, the use of the oxazoline homopolymer provided somewhat inferior results with regard to the absorption capacity and the blocking ratio both under a load when compared with the use of the oxazoline copolymer in Example 5.

Example 7

Water-absorbing agent (7), of which the absorption capacity under no load, the absorption capacity under a load. and the blocking ratio under a load were 44 (g/g), 21 (g/g), and 83% respectively as shown in Table 1, was obtained in the same way as of Example 5 except that the amounts of the oxazoline copolymer, water, and isopropanol were changed to 0.2 weight parts, 3 weight parts, and 1 weight part respectively. Thus, the use of 0.2 weight parts of the oxazoline copolymer provided somewhat inferior results with regard to the absorption capacity and the blocking ratio both under a load when compared with the use of 0.8 weight parts of the oxazoline copolymer in Example 5.

Example 8

Water-absorbing agent (8), of which the absorption capacity under no load, the absorption capacity under a load. and the blocking ratio under a load were 36 (g/g), 34 (g/g), and 99% respectively as shown in Table 1, was obtained in the same way as of Example 7 except that 1 weight part of 1,4-butanediol which was also a crosslinking agent was added to the treating agent. Thus, the use of the polyhydric alcohol, as additional crosslinking agent, further enhanced the absorption capacity under a load, but provided somewhat inferior results with regard to the blocking ratio under a load.

Example 9

A mixed solution comprising 0.8 weight parts of oxazoline compound, 10 weight parts of water, and 8 weight parts of isopropanol was added to 100 weight parts of water-absorbent resin (3) as obtained in Referential Example 3, wherein the oxazoline compound was a copolymer comprising (2-isopropenyl-2-oxazoline)/(ethyl acrylate)/(ethyl methacrylate)=85/5/10 weight % (pH=8~9 as aqueous solution; weight-average molecular weight=about 100,000). The resultant mixture was heated at 185° C. for 60 minutes to obtain water-absorbing agent (9), of which the absorption capacity under no load, the absorption capacity under a load. and the blocking ratio under a load were 30 (g/g), 28 (g/g), and 24% respectively as shown in Table 1.

Example 10

A mixed solution comprising 0.4 weight parts of oxazoline compound, 20 weight parts of water, and 0.3 weight parts of surfactant ®Tween-60 (polyoxyethylene sorbitan monostearate, made by Kao Corporation) was added to 100 weight parts of water-absorbent resin (3) as obtained in Referential Example 3, wherein the oxazoline compound was a copolymer comprising (2-isopropenyl-2-oxazoline)/ (ethyl acrylate)/(ethyl methacrylate)/ (monomethoxypolyethylene glycol acrylate)=50/2/28/20 weight % (pH=8~9 as aqueous solution; weight-average molecular weight=about 100,000). The resultant mixture was heated at 150° C. for 60 minutes to obtain water-absorbing agent (10), of which the absorption capacity under no load, the absorption capacity under a load. and the blocking ratio under a load were 35 (g/g), 27 (g/g), and 15% respectively as shown in Table 1.

Example 11

Water-absorbing agent (11), of which the absorption capacity under no load, the absorption capacity under a load. and the blocking ratio under a load were 36 (g/g), 26 (g/g), and 11% respectively as shown in Table 1, was obtained by adding the mixed solution (containing 0.4 weight parts of oxazoline compound) and then heating the resultant mixture in the same way as of Example 10 except that the amounts of water and the surfactant ®Tween-60 in the mixed solution (containing 0.4 weight parts of oxazoline compound) were changed to 10 weight parts and 0.1 weight part respectively. Thus, the amount of water of 10 weight parts provided somewhat inferior results with regard to the absorption capacity under a load.

Example 12

Water-absorbing agent (12), of which the absorption capacity under no load, the absorption capacity under a load. and the blocking ratio under a load were 36 (g/g), 22 (g/g), and 3% respectively as shown in Table 1, was obtained by adding the mixed solution (containing 0.4 weight parts of oxazoline compound) and then heating the resultant mixture in the same way as of Example 10 except that the amounts of water and the surfactant ®Tween-60 in the mixed solution (containing 0.4 weight parts of oxazoline compound) were changed to 5 weight parts and 0.1 weight part respectively. Thus, the amount of water of 5 weight parts provided somewhat inferior results with regard to the absorption capacity under a load.

Example 13

A mixed solution comprising 2 weight parts of oxazoline compound, 5 weight parts of isopropyl alcohol, and 0.5 weight parts of polypropylene glycol (molecular weight= 700) was added to 100 weight parts of water-absorbent resin (3) as obtained in Referential Example 3, wherein the oxazoline compound was a copolymer comprising (2-isopropenyl-2-oxazoline)/(ethyl acrylate)/(ethyl methacrylate)/(monomethoxypolyethylene glycol acrylate)= 50/2/28/20 weight % (pH=8~9 as aqueous solution; weight-average molecular weight=about 100,000). Then, to the above water-absorbent resin, 50 weight parts of water was further added. The resultant mixture was heated at 150° C. for 3 hours to obtain water-absorbing agent (13), of which the absorption capacity under no load, the absorption capacity under a load. and the blocking ratio under a load were 34 (g/g), 27 (g/g), and 0% respectively as shown in Table 1. From this result, it would be understood that even if a large amount of water is used, the oxazoline compound (copolymer) brings about no deterioration of the properties, and is therefore favorably usable even for the hydrogel.

Example 14

Water-absorbing agent (14), of which the absorption capacity under no load, the absorption capacity under a load. and the blocking ratio under a load were 34 (g/g), 26 (g/g), and 0% respectively as shown in Table 1, was obtained by adding the mixed solution and then heating the resultant mixture in the same way as of Example 13 except that the amount of water as used was changed to 100 weight parts. From this result, similarly to Example 13, it would be understood that even if a large amount of water is used, the oxazoline compound (copolymer) brings about no deterioration of the properties.

Example 15

In Example 1, one hundred weight parts of water-absorbent resin (1) was mixed with 2 weight parts of oxazoline emulsion, 20 weight parts of water, and 0.3 weight parts of the surfactant ®Tween-60, wherein the oxazoline emulsion comprised (butyl acrylate)/(styrene)/(divinylbenzene)/(isopropenyloxazoline)=79.4/0.5/0.1/20 in weight ratio. The resultant mixture was heated in the same way as of Example 1, thus obtaining water-absorbing agent (15), of which the absorption capacity under no load, the absorption capacity under a load. and the blocking ratio under a load were 34 (g/g), 26 (g/g), 0% respectively as shown in Table 1.

Comparative Example 1

One hundred weight parts of water-absorbent resin (2), as obtained in Referential Example 2, was mixed with a treating agent comprising 1 weight part of glycerol, 3 weight parts of water, and 1 weight part of isopropyl alcohol. The resultant mixture was heated at 210° C. for 40 minutes to obtain comparative water-absorbing agent (1), of which the absorption capacity under no load, the absorption capacity under a load. and the blocking ratio under a load were 32 (g/g), 26 (g/g), and 99% respectively as shown in Table 1.

Comparative Example 2

One hundred weight parts of water-absorbent resin (2), as obtained in Referential Example 2, was mixed with a treating agent comprising 0.1 weight part of ethylene glycol diglycidyl ether, 3 weight parts of water, and 1 weight part of isopropyl alcohol. The resultant mixture was heated at 210° C. for 40 minutes to obtain comparative water-absorbing agent (2), of which the absorption capacity under no load, the absorption capacity under a load. and the blocking ratio under a load were 34 (g/g), 27 (g/g), and 56% respectively as shown in Table 1.

Comparative Example 3

Comparative water-absorbing agent (3), of which the absorption capacity under no load, the absorption capacity under a load. and the blocking ratio under a load were 55 (g/g), 8 (g/g), and 52% respectively as shown in Table 1, was obtained in the same way as of Example 1 except that water-absorbent resin (1) was replaced with a basic water-absorbent resin having a neutralization ratio of 98% (pH= 7.7). From this result, it would be understood that, even if the same oxazoline compound is used, he basic water-absorbent resin involves the difficulty to improve the absorption capacity under a load or the blocking ratio under a load.

TABLE 1

|  | Water-absorbing agent | Absorption capacity under no load (g/g) | Absorption capacity under load (g/g) | Blocking ratio under load (%) |
| --- | --- | --- | --- | --- |
| Examples | (1) | 31 | 27 | 0 |
|  | (2) | 36 | 28 | 0 |
|  | (3) | 36 | 26 | 0 |
|  | (4) | 37 | 25 | 0 |
|  | (5) | 43 | 25 | 33 |
|  | (6) | 44 | 21 | 83 |
|  | (7) | 44 | 21 | 83 |
|  | (8) | 36 | 34 | 99 |
|  | (9) | 30 | 28 | 24 |
|  | (10) | 35 | 27 | 15 |
|  | (11) | 36 | 26 | 11 |
|  | (12) | 36 | 22 | 3 |
|  | (13) | 34 | 27 | 0 |
|  | (14) | 34 | 26 | 0 |
|  | (15) | 34 | 26 | 0 |
| Comparative Examples | (1) | 32 | 26 | 99 |
|  | (2) | 34 | 27 | 56 |
|  | (3) | 55 | 8 | 52 |

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A water-absorbing agent, which is obtained by a process including the steps of mixing a water-absorbent resin with an oxazoline compound and thereby making a crosslinking treatment of the water-absorbent resin with the oxazoline compound and has an absorption capacity of not less than 30 (g/g) under no load and an absorption capacity of not less than 25 (g/g) under a load.

2. A water-absorbing agent according to claim 1, which has an average particle size of 200 to 600 µm in diameter and contains fine particles with a particle size of not greater than 150 µm in diameter in the ratio of not higher than 10 weight %.

3. A water-absorbing agent according to claim 1, which has a pH of not higher than 6.0 in physiological saline.

4. A water-absorbing agent according to claim 1, which has a blocking ratio of not higher than 20 weight % under a load.

5. A water-absorbing agent according to claim 1, wherein the oxazoline compound has at least three structural units of general formula (1) below:

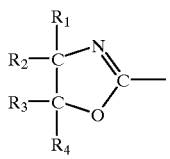

(1)

wherein $R_1$ to $R_4$ separately denote a hydrogen atom, an alkyl group, an aromatic group, a halogen group, a substituted alkyl group, or a substituted aromatic group.

6. A water-absorbing agent according to claim 1, wherein the water-absorbent resin is an acidic water-absorbent resin, and the oxazoline compound is a basic oxazoline compound.

7. A water-absorbing agent according to claim 1, wherein the oxazoline compound is more basic than the water-absorbent resin.

8. A water-absorbing agent, which is obtained by a process including the steps of mixing 100 weight parts of a water-absorbent resin with 0.001 to 10 weight parts of an oxazoline compound and thereby making a crosslinking treatment of the water-absorbent resin with the oxazoline compound, wherein the oxazoline compound has at least three structural units of general formula (1) below:

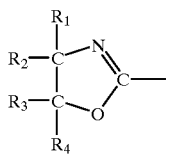

(1)

wherein $R_1$ to $R_4$ separately denote a hydrogen atom, an alkyl group, an aromatic group, a halogen group, a substituted alkyl group, or a substituted aromatic group.

9. A water-absorbing agent according to claim 8, wherein the oxazoline compound is a copolymer.

10. A water-absorbing agent according to claim 8, wherein the oxazoline compound is more basic than the water-absorbent resin.

11. A water-absorbing agent, which comprises 100 weight parts of an acidic water-absorbent resin and 0.001 to 10 weight parts of a basic oxazoline compound.

12. A water-absorbing agent according to claim 11, which has an absorption capacity of not less than 30 (g/g) under no load and an absorption capacity of not less than 25 (g/g) under a load.

13. A water-absorbing agent according to claim 11, wherein the oxazoline compound has at least three structural units of general formula (1) below:

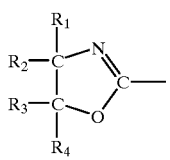

(1)

wherein $R_1$ to $R_4$ separately denote a hydrogen atom, an alkyl group, an aromatic group, a halogen group, a substituted alkyl group, or a substituted aromatic group.

14. A water-absorbing agent according to claim 11, which has an absorption capacity of not less than 25 (g/g) under a load and a blocking ratio of not higher than 20 weight % under a load.

15. A water-absorbing agent, which comprises 100 weight parts of a water-absorbent resin and 0.001 to 10 weight parts of an oxazoline compound having at least three structural units of general formula (1) below:

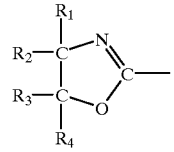

(1)

wherein $R_1$ to $R_4$ separately denote a hydrogen atom, an alkyl group, an aromatic group, a halogen group, a substituted alkyl group, or a substituted aromatic group.

16. A water-absorbing agent according to claim 15, which has an absorption capacity of not less than 30 (g/g) under no load and an absorption capacity of not less than 25 (g/g) under a load.

17. A water-absorbing agent according to claim 15, wherein the oxazoline compound is more basic than the water-absorbent resin.

18. A water-absorbing agent according to claim 15, which has an absorption capacity of not less than 25 (g/g) under a load and a blocking ratio of not higher than 20 weight % under a load.

19. A water-absorbing agent, which is obtained by a process including the steps of mixing a water-absorbent resin with an oxazoline compound and thereby making a crosslinking treatment of the water-absorbent resin with the oxazoline compound, and has an absorption capacity of not less than 25 (g/g) under a load and a blocking ratio of not higher than 20 weight % under a load.

20. A water-absorbing agent according to claim 19, wherein the oxazoline compound has at least three structural units of general formula (1) below:

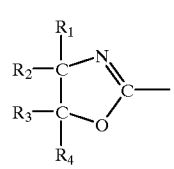

(1)

wherein $R_1$ to $R_4$ separately denote a hydrogen atom, an alkyl group, an aromatic group, a halogen group, a substituted alkyl group, or a substituted aromatic group.

21. A water-absorbing agent according to claim 19, wherein the water-absorbent resin is an acidic water-absorbent resin, and the oxazoline compound is a basic oxazoline compound.

22. A water-absorbing agent according to claim 19, wherein the oxazoline compound is more basic than the water-absorbent resin.

23. A water-absorbing agent according to claim 19, which has a blocking ratio of not higher than 20 weight % under a load.

* * * * *